US009360412B2

(12) United States Patent
Kelley

(10) Patent No.: US 9,360,412 B2
(45) Date of Patent: Jun. 7, 2016

(54) ROTATING OPTICS FOR MULTIPLE CUVETTE ARRAY

(71) Applicant: Mark Kelley, St. Paul, MN (US)

(72) Inventor: Mark Kelley, St. Paul, MN (US)

(73) Assignee: Honeywell International Inc., Morris Plains, NJ (US)

( * ) Notice: Subject to any disclaimer, the term of this patent is extended or adjusted under 35 U.S.C. 154(b) by 183 days.

(21) Appl. No.: 13/678,990

(22) Filed: Nov. 16, 2012

(65) Prior Publication Data

US 2014/0139832 A1 May 22, 2014

(51) Int. Cl.
*G01N 21/03* (2006.01)
*G01N 21/01* (2006.01)

(52) U.S. Cl.
CPC ...................................... *G01N 21/01* (2013.01)

(58) Field of Classification Search
CPC .......... G01N 21/05; G01N 2021/0346; G01N 21/03; G01N 21/01; G01N 30/74; G01N 21/0303; G01N 21/253; G01N 21/645; G01N 21/07; G01N 2021/6482; G01N 35/025
USPC ............. 356/246, 440, 244, 39, 36, 410, 432, 356/73, 441, 51
See application file for complete search history.

(56) References Cited

U.S. PATENT DOCUMENTS

| | | | | |
|---|---|---|---|---|
| 3,441,383 A * | 4/1969 | Moore | .................. | B01L 3/5085 206/459.5 |
| 4,123,173 A * | 10/1978 | Bullock et al. | ................. | 356/246 |
| 4,234,540 A * | 11/1980 | Ginsberg et al. | ................. | 422/64 |
| 4,430,299 A * | 2/1984 | Horne | .............................. | 422/64 |
| 4,456,581 A * | 6/1984 | Edelmann et al. | .............. | 422/72 |
| 4,477,190 A | 10/1984 | Liston et al. | | |
| 5,075,077 A * | 12/1991 | Durley et al. | .................. | 422/424 |
| 5,721,384 A * | 2/1998 | Tanihata | ............ | G01N 35/0099 73/864.81 |
| 5,741,634 A | 4/1998 | Nozoe et al. | | |
| 5,827,744 A * | 10/1998 | Fose et al. | ........................ | 436/49 |
| 5,935,785 A * | 8/1999 | Reber et al. | .................. | 435/6.11 |
| 6,203,760 B1 * | 3/2001 | van der Plaats et al. | ......... | 422/63 |
| 6,518,056 B2 * | 2/2003 | Schembri et al. | ........... | 435/287.2 |
| 6,823,278 B1 * | 11/2004 | Carney et al. | ................... | 702/94 |
| 8,574,895 B2 * | 11/2013 | Freeman et al. | ........... | 435/288.7 |
| 2004/0265173 A1* | 12/2004 | Matsumoto et al. | ............ | 422/64 |
| 2008/0003696 A1* | 1/2008 | Rae | ........................ | G01N 21/03 436/514 |
| 2011/0093207 A1* | 4/2011 | Ingber et al. | ..................... | 702/19 |
| 2011/0194114 A1* | 8/2011 | Yeo | ................................ | 356/435 |

FOREIGN PATENT DOCUMENTS

| | | |
|---|---|---|
| EP | 353590 A2 | 2/1990 |
| EP | 353590 B1 | 4/1996 |
| EP | 1218720 A1 | 7/2002 |
| EP | 1441637 A1 | 8/2004 |
| EP | 1779109 B1 | 1/2012 |

OTHER PUBLICATIONS http://www.thesaurus.com/browse/corresponding+to.*

* cited by examiner

*Primary Examiner* — Tarifur Chowdhury
*Assistant Examiner* — Mohamed K Amara
(74) *Attorney, Agent, or Firm* — Schwegman Lundberg & Woessner, P.A.

(57) ABSTRACT

A system includes a testing instrument to hold a test card having multiple cuvettes radially spaced about a point on the card. A rotatable mount is supported in relation the point on the card when the card is held in the testing system. Optics are supported on the rotatable mount to provide radiation to the multiple cuvettes.

20 Claims, 4 Drawing Sheets

ROTATING OPTICS FOR MULTIPLE CUVETTE ARRAY

BACKGROUND

Multiple cuvettes may be used on test cards to hold samples of biological fluids that need to be tested. The test cards may be inserted into an instrument to conduct the tests using various sensors. Such instruments can be expensive.

SUMMARY

A system includes a testing instrument to hold a test card having multiple cuvettes radially spaced about a point on the card. A rotatable mount is supported in relation to the point on the card when the card is held in the testing system. Optics are supported on the rotatable mount to provide radiation to the multiple cuvettes.

A system includes a testing instrument to hold a test card having multiple cuvettes radially spaced about a point on the card. Multiple light emitting diodes are supported in the system to rotate with respect to the point on the card when held, the multiple light emitting diodes to provide multiple different frequencies of light to the multiple cuvettes.

A method includes receiving a card into a test instrument to hold the card in a fixed position within the test instrument, the card having multiple cuvettes to hold samples, the card being transparent to light, rotating optics to provide light to selected cuvettes, and detecting light from the optics through the selected cuvettes.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical, optical, and electrical changes may be made without departing from the scope of the present invention. The following description of example embodiments is, therefore, not to be taken in a limited sense, and the scope of the present invention is defined by the appended claims.

A test instrument receives a disposable test card that contains many layers of a transparent material such as PET or other acrylic or suitable material that can be pattered with various liquid fluid transport features. The card may be used to position samples in cuvettes using a small volume of liquid, with the test instrument performing one or more tests. The liquid, such as blood, to be tested, may be transported via one or more layers of the test card, and prepared for analysis by a test instrument into which the card is inserted. Various sensors, such as a combination of light emitting diodes and photoreceptors may be used to test the liquid.

Figure 1:
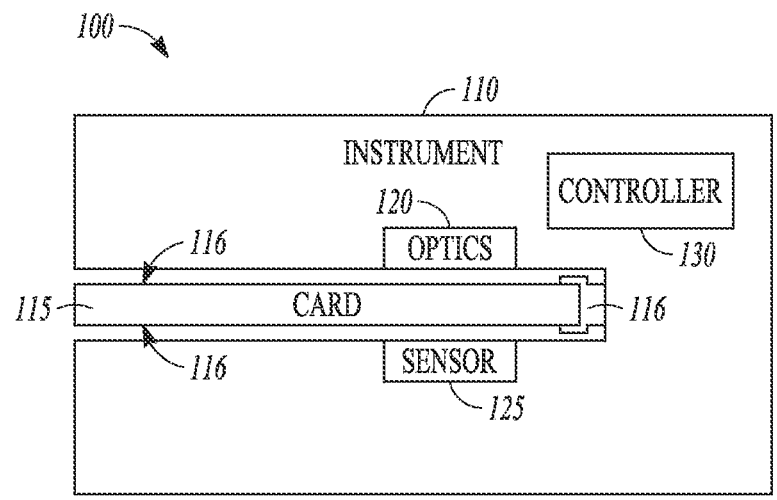
FIG. 1 is a block diagram of a test instrument having a test card for sensing samples on the test card according to an example embodiment.

FIG. 1 is a block diagram of a system 100 that includes a test instrument 110 with a removable test card 115 for sensing samples on the test card 115 according to an example embodiment. The test card may be held in the test system when inserted by one or more guides 116 to hold the card in a selected position. When the card 115 is in the selected position as shown, rotatable optics 120 are positioned relative to the card 115 and are used to provide light to samples on the card 115 and a sensor 125 is positioned to receive and detect light transmitted through the samples on the card. The sensor 125 provides information regarding the detected light to a controller 130. The controller 130 controls rotation of the optics 120 such that light of a selected frequency is utilized for different samples. The optics 120 may be rotated to obtain a desired frequency of light for each sample. In further embodiments, the sensor 125 may include multiple detectors that may also be rotated by the controller 130 such that one or more detectors on the sensor 125 may be configured to better detect the selected frequencies of light.

Figure 2:
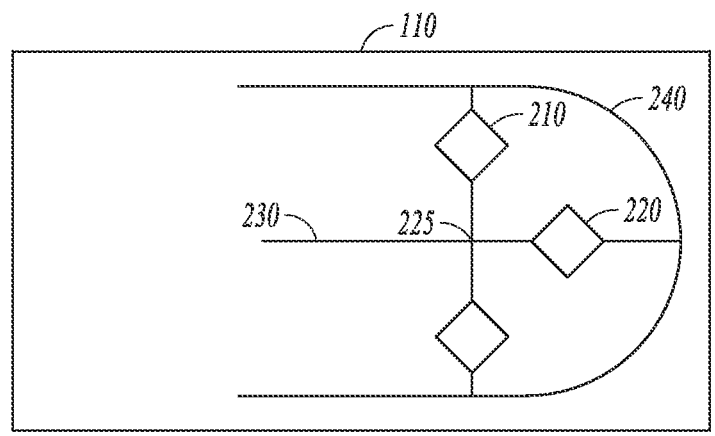
FIG. 2 is a block schematic diagram of a top of a test card showing multiple cuvettes containing samples to be sensed according to an example embodiment.

FIG. 2 is a simplified block schematic diagram of a top of test card 115 showing multiple cuvettes 210, 215, 220 containing samples to be sensed according to an example embodiment. The cuvettes 210, 215, 220 are radially spaced from a center point 225, with each cuvette being shown at the same radial distance from the center point 225. While three cuvettes are shown, there may be many more in further embodiments, or fewer. In further embodiments, the cuvettes may be different distances from the center point 225. In still further embodiments, many more cuvettes may be located at different radial distances. The cuvettes may be filled with samples by any means, such as channels 230 from another point on the card 115, or may be provided to the cuvettes directly from off the card 115.

In an example embodiment, the sample flows around an outer ring like channel 240, over reagent stored on card 115 on entry or in a cuvette. The sample may be driven by applying a vacuum to the center 225 where a gas permeable membrane may be placed. This ensures that all cuvettes are filled so long as there is sufficient sample. The filling of cuvettes with sample may be done in other manners in further embodiments.

Figure 3:
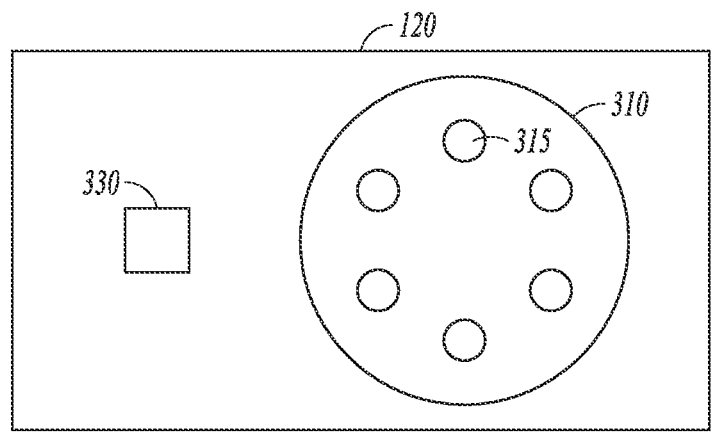
FIG. 3 is a block schematic diagram of a rotational mount with multiple optics used to provide different frequency light to the samples of FIG. 2 according to an example embodiment.

FIG. 3 is a block schematic diagram of optics 120, including a rotational mount 310 with multiple optics 315, 320, 325 used to provide different frequency light to the samples in the cuvettes 210, 215, 220 of FIG. 2 according to an example embodiment. In one embodiment, two or three such optics are provided, and may include light emitting diodes (LEDs) that each emit a selected frequency of light. In the embodiment shown, there are six LEDs arranged in a hexagonal pattern, each having the same distance from a center corresponding to the center point 225 of the cuvettes when the card is registered in test instrument 100. The frequency of each LED may be selected to optimize detection of appropriate samples.

In one embodiment, there may be many more cuvettes than shown in FIG. 2 that can be sensed using just a few LEDs to provide a compact testing capability. Additional LEDs to test a few cuvettes may be appropriate if the test instrument 100 is to be configured for many different test cards where a wide range of wavelengths may be desirable. Similarly, the number of detectors in sensor 125 may be selected to not exceed the number of cuvettes. In one embodiment, all detectors may be hard mounted and are there to detect the response from each cuvette. If the detectors are mounted on a rotating stage, as are the LEDs, even fewer detectors may be used.

In one embodiment, the optics are radially spaced and angularly spaced from each other to allow alignment with the proper cuvette on the card 115. Multiple additional LEDs are illustrated on optics 120, forming different radially spaced sets of LEDs to be used for each cuvette at the corresponding radial spacing, either at the same time, or sequentially. The frequencies and other parameters of the sets of LEDs may be configured and varied between each LED in a set for the particular cards and tests to be run on samples on the cards. Any sample at the same radius may be tested using light from any one of the LEDs in the corresponding set by simply rotating the set until the desired LED is positioned to provide light through that sample.

In one embodiment, a sensor 330 may be used to detect the position of the rotational mount 310. The sensor may be located outside the radius of the rotating mount, or supported on the test instrument to detect the position of the rotating mount and provide feedback to the controller. Power may be provided to LEDs on the rotational mount 310 by wires, and the mount may be controlled to rotate in either direction an amount sufficient to obtain all desired rotational positions without unduly stressing the wires. Other means of providing power to the LEDs may be provided in further embodiments.

Figure 4:
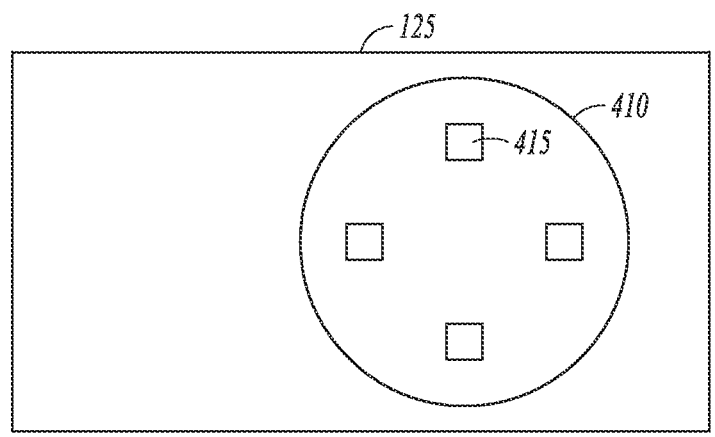
FIG. 4 is a block schematic diagram of a set of sensors to sense light projected through samples according to an example embodiment.

FIG. 4 is a block schematic diagram of a sensor 125, which may optionally be rotatable as shown at 410. The sensor 125 includes one or more detectors 415, 420, 425 to sense light projected through samples according to an example embodiment. Four detectors are shown in FIG. 4, again arranged to receive light through samples in the cuvettes in the card 115 when registered in the test instrument. The detectors in one embodiment may be fixed in relation to the cuvettes, or may be rotatable. In one embodiment, the wavelengths to be detected are in the visible spectrum, allowing use of one or more different types of photodetectors to provide adequate sensing capabilities. In further embodiments, additional types of detectors may also be used to provide for different light that is expected to be detected. The frequency of each LED and detector may be selected to optimize detection of appropriate samples. In one embodiment, the detectors are radially spaced and angularly spaced from each other to allow alignment with the proper cuvette on the card 115. Multiple additional detectors are illustrated on sensor 125, forming different radially spaced sets of detectors to be used for each cuvette at the corresponding radial spacing, either at the same time, or sequentially. The frequencies and other parameters of the sets of detectors may be configured and varied between each detector in a set for the particular cards and tests to be run on samples on the cards.

Figure 5:
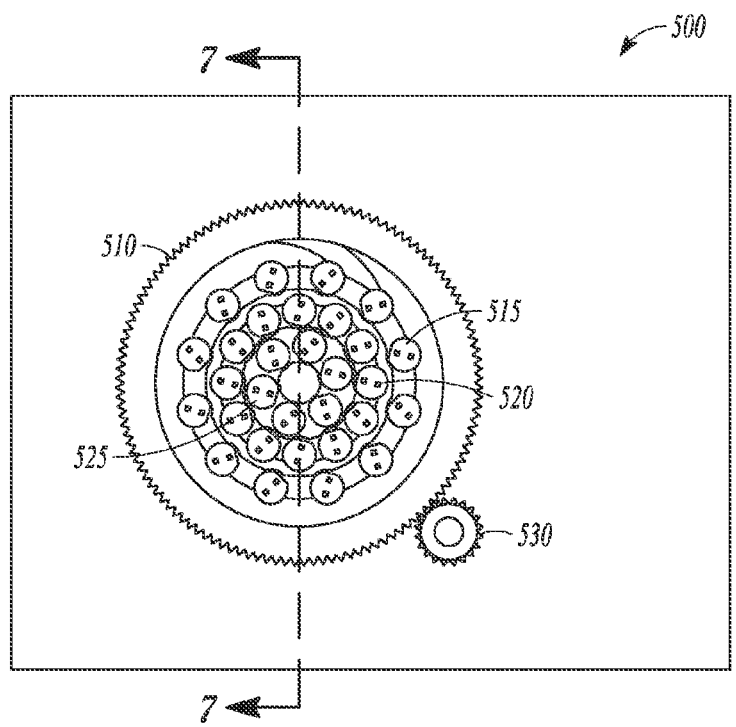
FIG. 5 is a block schematic diagram of a rotatable set of LEDs having different frequencies according to a further example embodiment.

FIG. 5 is a block schematic diagram of optics 500 including a rotatable set of LEDs having different frequencies according to a further example embodiment. A turntable 510 or other rotatable structure is populated with multiple LEDs arranged in sets at different radii as indicated at 515, 520, 525. In one example, set 515 is located at a diameter of 1.5, set 520 at 1.0, and set 525 at radius 0.5, forming concentric circles of sets of LEDs. The radii may vary in further embodiments. As indicated above, each set of LEDs may include LEDs having different characteristics, such as frequency and intensity in order to be used to provide light through samples at the selected radius of the set. Thus any sample at the same radius may be tested using light from any one of the LEDs in the corresponding set by simply rotating the set until the desired LED is positioned to provide light through that sample.

In one embodiment, each set of LEDs at each radius may have the same frequency. This allows the design of the card to place cuvettes containing selected sample at a radius corresponding to the desired frequency for testing. The LEDs may than be rotated to align with each cuvette. In a further embodiment, the properties of LEDs within a set may be correlated with LEDs in further sets at different radii in order to test multiple samples at different radii in a single step, without having to place all samples of a selected frequency at the same radius. The rotation of the LEDs would then allow for a cuvette to be interrogated by many different wavelengths during the course of testing. Many tests may involve two wavelengths repeatedly flashing to correct for various factors. In other embodiments, samples may be tested sequentially, moving the optics between each test to obtain the desired light characteristics for that sample. However, given one or more cards with known sample positions, the LEDs may be positioned to provide desired light for multiple samples in one rotational position.

In one embodiment, the controller 130 controls a stepper motor represented by a drive gear 520 to rotate turntable 510, which contains mating gears. In further embodiments, the motor may be directly coupled to turn the turntable about its central axis, which is positioned centrally with respect to the center point 225 of a registered card 115. In one embodiment, the motor may be provided with an encoder to control the position and motion of the turntable 510. The controller may be provided external information to properly position the optics for a card to be tested, or may receive information from directly from the card. RFID, bar codes, QR codes, or other information may be read from a card by the test instrumentation 110 to properly position the sensor 120. Image analysis may be used in further embodiments to position the sensor 120.

In a further embodiment, rotation of the LEDs provides the ability to sweep a lit LED through a cuvette and pull max value seen by a static aligned detector without the need for static alignment of the LED.

Figure 6:
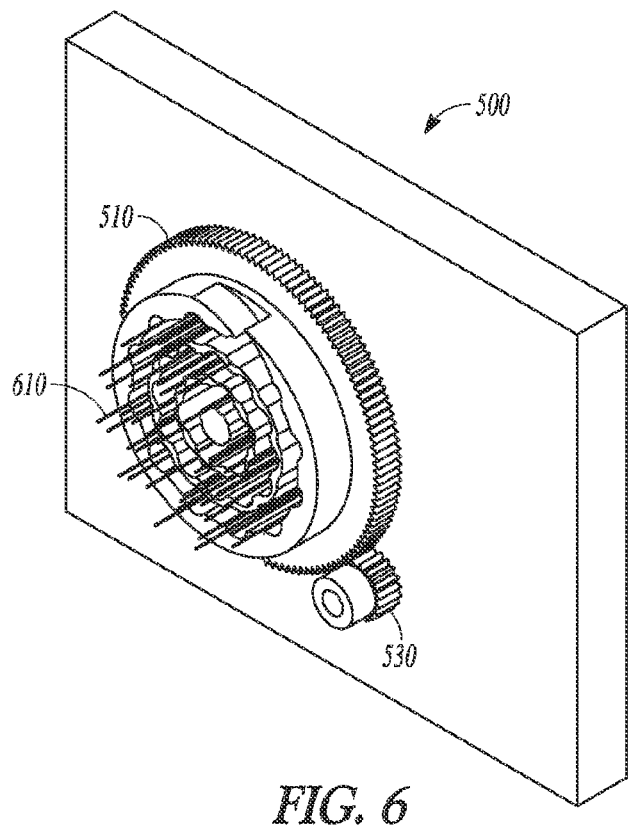
FIG. 6 is a perspective view of the rotatable set of LEDs of FIG. 5.

FIG. 6 is a perspective view of the rotatable set of LEDs of FIG. 5. Electrical leads 610 used to power the LEDs are illustrated. In further embodiments, optical fibers from the LEDs may be used to direct the light from each LED toward a sample. A carrier cable 620 is also shown, which may be used to bundle and route wires outside of the turntable 510.

Figure 7:
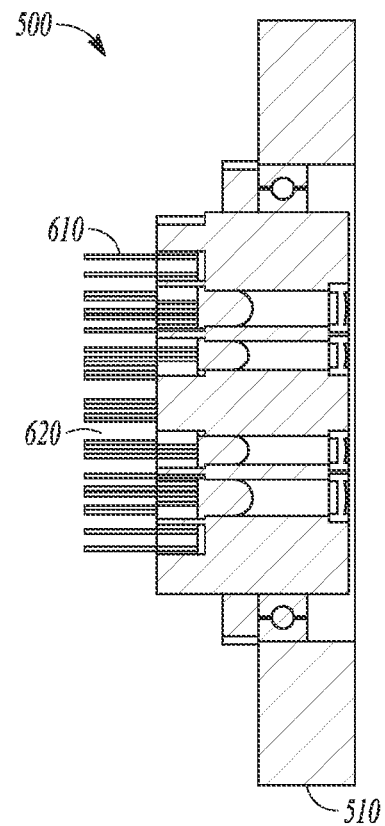
FIG. 7 is a cross section view of the rotatable set of LEDs taken along line 6-6 in FIG. 5 according to an example embodiment.

FIG. 7 is a cross section view of the rotatable set of LEDs taken along line 6-6 in FIG. 5 according to an example embodiment.

Figure 8:
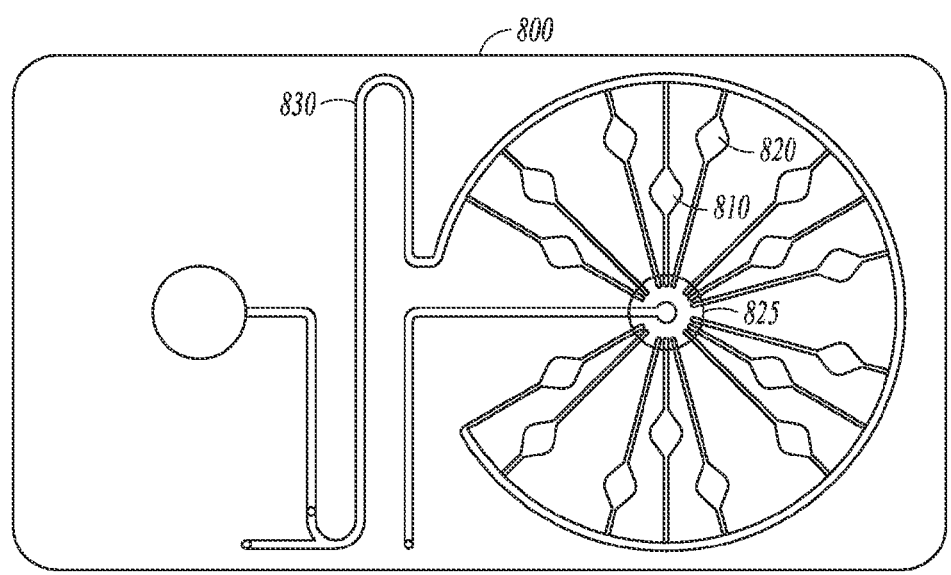
FIG. 8 is a block schematic top view of a test card having a set of cuvettes to hold samples for testing according to an example embodiment.

FIG. 8 is a block schematic top view of a test card 800 having a set of cuvettes to hold samples for testing according to an example embodiment. In one embodiment, two sets of cuvettes 810 and 820 are shown, each set having a different radius from a center 825. They are filled via a channel 830. This embodiment illustrates that many different cuvettes may be included and contain samples to be tested.

Examples

1. A system comprising:
a testing instrument to hold a removable test card having multiple cuvettes radially spaced about a point on the card;
a rotatable mount supported in relation to the point on the card when the card is held in the testing instrument; and
optics supported on the rotatable mount to provide radiation to the multiple cuvettes.

2. The system of example 1 wherein the optics comprises multiple optics to provide radiation having different frequencies.

3. The system of example 2 and further comprising an encoded motor coupled to the rotatable mount to selectively rotate the optics to provide different frequencies of radiation to the multiple cuvettes.

4. The system of any of examples 1-3 and further comprising a detector supported by the test fixture on a side of the card opposite the optics to receive radiation from the optics through selected cuvettes.

5. The system of example 4 wherein the detector comprises a rotatable detector.

6. The system of example 4 wherein the detector comprises multiple rotatable detectors.

7. The system of example 6 wherein the multiple rotatable detectors comprise detectors having different frequency sensitivities.

8. The system of example 4 and further comprising optics to direct light received through each cuvette to the detector.

9. The system of any of examples 1-8 wherein the optics include multiple LED having different frequencies of light emission.

10. The system of example 9 wherein the optics are arranged in concentric circles about the point.

11. The system of any of examples 1-10 wherein the optics comprise lenses optically coupled to a light source.

12. A system comprising:
a testing instrument to hold a removable test card having multiple cuvettes radially spaced about a point on the card;
multiple light emitting diodes supported in the testing instrument to rotate with respect to the point on the card when held, the multiple light emitting diodes to provide multiple different frequencies of light to the multiple cuvettes.

13. The system of example 12 and further comprising a detector supported on a side of the card opposite the light emitting diodes to receive radiation from the light emitting diodes through selected cuvettes.

14. The system of example 13 wherein the detector comprises multiple rotatable detectors to detect different frequencies of light.

15. A method comprising:
receiving a card into a test instrument to hold the card in a fixed position within the test instrument, the card having multiple cuvettes to hold samples, the card being transparent to light;
rotating optics to provide light to selected cuvettes; and
detecting light from the optics through the selected cuvettes.

16. The method of example 15 wherein the optics comprise a light emitting diode.

17. The method of any of examples 15-16 and further comprising rotating the optics to provide different frequencies of light to selected cuvettes.

18. The method of example 17 wherein the different frequencies of light are provided by multiple light emitting diodes having different frequencies of light emission.

19. The method of any of examples 15-18 wherein detecting light comprises rotating a light detector to different positions to receive light through the selected cuvettes.

20. The method of any of examples 15-19 wherein detecting light comprises rotating multiple light detectors to different positions to receive light through the selected cuvettes.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A system comprising:
a testing instrument to hold, in a selected fixed position, a removable multilayer transparent test card having multiple cuvettes equally radially spaced about a center axis on the test card;
a rotatable mount coaxially supported with the center axis of the transparent test card when the card is held in the testing instrument; and
optics supported on the rotatable mount that rotates coaxially with the center axis, the optics radially spaced a fixed distance from the center axis to provide radiation to the multiple cuvettes by rotating to different positions around the center axis of the transparent test card such that the optics move to positions corresponding to the multiple cuvettes.

2. The system of claim 1 wherein the optics comprises multiple optics to provide radiation having different frequencies.

3. The system of claim 2 and further comprising an encoded motor coupled to the rotatable mount to selectively rotate the optics to provide different frequencies of radiation to the multiple cuvettes.

4. The system of claim 1 and further comprising a detector supported by the testing instrument on a side of the card opposite the optics to receive radiation from the optics through selected cuvettes.

5. The system of claim 4 wherein the detector comprises a rotatable detector.

6. The system of claim 4 wherein the detector comprises multiple rotatable detectors.

7. The system of claim 6 wherein the multiple rotatable detectors comprise detectors having different frequency sensitivities.

8. The system of claim 4 and further comprising optics to direct light received through each cuvette to the detector.

9. The system of claim 1 wherein the optics include multiple LED having different frequencies of light emission.

10. The system of claim 9 wherein the optics are arranged in concentric circles about the center axis.

11. The system of claim 1 wherein the optics comprise lenses optically coupled to a light source.

12. A system comprising:
a testing instrument to hold, in a selected fixed position, a removable multilayer transparent test card having multiple cuvettes equally radially spaced about a center axis on the card;
multiple light emitting diodes supported in the testing instrument and radially spaced a fixed distance from the center axis to rotate around the center axis of the transparent test card when held, the multiple light emitting diodes to provide multiple different frequencies of light to the multiple cuvettes by rotating to different positions around the center axis of the transparent test card such that the light emitting diodes move to positions corresponding to the multiple cuvettes.

13. The system of claim 12 and further comprising a detector supported on a side of the card opposite the light emitting diodes to receive radiation from the light emitting diodes through selected cuvettes.

14. The system of claim 13 wherein the detector comprises multiple rotatable detectors to detect different frequencies of light.

15. A method comprising:
receiving a multilayer card into a test instrument to hold the card in a fixed position within the test instrument, the card having multiple cuvettes equally radially spaced about a center axis on the card to hold samples, the card being transparent to light;
rotating optics coaxial with and radially spaced a fixed distance from the center axis to different positions around the center axis of the transparent test card to provide light to selected cuvettes such that the optics move to positions corresponding to the multiple cuvettes; and
detecting light from the optics through the selected cuvettes.

16. The method of claim 15 wherein the optics comprise a light emitting diode.

17. The method of claim 15 and further comprising rotating the optics to provide different frequencies of light to selected cuvettes.

18. The method of claim 17 wherein the different frequencies of light are provided by multiple light emitting diodes having different frequencies of light emission.

19. The method of claim 15 wherein detecting light comprises rotating a light detector to different positions to receive light through the selected cuvettes.

20. The method of claim 15 wherein detecting light comprises rotating multiple light detectors to different positions to receive light through the selected cuvettes.

* * * * *